United States Patent
Phillips et al.

(10) Patent No.: US 6,809,081 B1
(45) Date of Patent: Oct. 26, 2004

(54) CHEMOTHERAPEUTIC COMPOSITION AND METHOD

(75) Inventors: Nigel C. Phillips, Pointe-Claire (CA); Mario C. Filion, Laval (CA)

(73) Assignee: Bioniche Life Sciences, Inc., Quebec (CA)

( * ) Notice: Subject to any disclaimer, the term of this patent is extended or adjusted under 35 U.S.C. 154(b) by 0 days.

(21) Appl. No.: 09/857,332

(22) PCT Filed: Dec. 3, 1999

(86) PCT No.: PCT/CA99/01157

§ 371 (c)(1),
(2), (4) Date: Sep. 17, 2001

(87) PCT Pub. No.: WO00/33875

PCT Pub. Date: Jun. 15, 2000

Related U.S. Application Data

(60) Provisional application No. 60/127,320, filed on Apr. 1, 1999, and provisional application No. 60/111,019, filed on Dec. 4, 1998.

(51) Int. Cl.[7] .............................................. A61K 48/00
(52) U.S. Cl. ............................. 514/44; 514/1; 435/243; 536/23.1
(58) Field of Search ....................... 514/1, 44; 435/243, 435/253; 536/23.1; 424/434, 92–94

(56) References Cited

U.S. PATENT DOCUMENTS

| | | | |
|---|---|---|---|
| 5,759,554 A | * | 6/1998 | Alkemade et al. |
| 6,326,357 B1 | | 12/2001 | Phillips et al. |
| 6,329,347 B1 | | 12/2001 | Phillips et al. |

FOREIGN PATENT DOCUMENTS

| WO | WO 99 07383 A2 | 2/1999 |
|---|---|---|

OTHER PUBLICATIONS

S Yamamoto et al., Jpn.J. Cancer Res., "In vitro Augmentation of Natural Killer Cell Activity and Production of Interfon and a/b and with Deoxyribonucleic Acid Fraction from Mycobacterium bovis BCG," Jul. 1988. 79, pp. 866–873.*

A Morales et al., Journal of Urology. "Immunotherapy of an Experimental Adenocarcinoma of the Prostate." May 1995. vol. 153 pp. 1706–1710.*

Database Biosis Online, Biosciences Information Service, Philadelphia, PA, US Filion, M.C., et al., "Mycobacterial cell wall–DNA complex induced apoptosis in cancer cells". (Sep. 1998), XP002133100. Journ. of Pharmacy and Pharmacology, 135th Meeting of the British Pharmaceutical Conference Eastbourne, England, UK Sep. 8–11, 1998, p. 39, vol. 50.

Filion, et al., "Toxicity and immunomodulatory activity of liposomal vectors formulated with cationic lipids toward immune effector cells", Biochim Biophys Acta, 1997, 345–356, vol. 1329.

Phillips, et al., "Influence of phospholipid compositions on antibody responses to liposome encapsulated protein and peptide antigens". Vaccine, 1996, pp. 898–904, vol. 14 No. 9.

Fillion, M.C., et al., "Mycobacterial DNA induces apoptosis in myeloid leukemia cell lines", Thirty–Ninth Annual Meeting of the American Society of Hematology, San Diego, California, USA, Dec. 5–9, 1997, Blood, vol. 90 (10 Suppl. 1 part 2).

Fillion, M.C., et al., "Mycobacterium phlei cell wall complex, a new anti–tumoral agent, induces IL–12 synthesis by monocyte–macrophages via associated DNA", Thirty–Ninth Annual Meeting of the American Society of Hematology, San Diego, California, USA, Dec. 5–9, 1997, Blood, vol. 90 (10 Suppl. 1 part 2).

Yamamoto, S., et al., "*In vitro* Augmentation of Natural Killer Cell Activity and Production of Interferon–α/β and –γ with Deoxyribonucleic Acid Fraction from *Mycobacterium bovis* BCG", Jpn. J. Cancer Res., Jul. 1988, pp. 866–873, vol. 79 (XP–002085535).

* cited by examiner

Primary Examiner—Dave T. Nguyen
Assistant Examiner—J. Eric Angell
(74) Attorney, Agent, or Firm—Kilpatrick Stockton LLP

(57) ABSTRACT

The present invention relates to a composition and method comprising *Mycobacterium phlei* (*M. phlei*)-DNA (M-DNA), M-DNA preserved and complexed on *M. phlei* cell wall (MCC), a chemotherapeutic agent and a pharmaceutically acceptable carrier, wherein the M-DNA and the MCC induce cell cycle arrest in proliferating cancer cells, inhibit proliferation of cancer cells, induce apoptosis in cancer cells and potentiate the antineoplastic effect of the chemotherapeutic agent on cancer cells.

32 Claims, 9 Drawing Sheets

INDUCTION OF APOPTOSIS IN B16 MELANOMA CELLS

1. M.DNA 1 µg/ml
2. MCC 100 µg/ml
3. MCC 10 µg/ml
4. MCC 1 µg/ml
5. Control cells
L. DNA ladder

CHEMOTHERAPEUTIC COMPOSITION AND METHOD

CROSS REFERENCE TO RELATED APPLICATIONS

This application claims priority to PCT/CA99/01157 filed Dec. 3, 1999 which claims priority to U.S. Provisional Application Ser. No. 60/111,019 filed Dec. 4, 1998 and to U.S. Provisional Application Ser. No. 60/127,320 filed Apr. 1, 1999.

FIELD OF INVENTION

The present invention relates to a composition and method comprising *Mycobacterium phlei* (*M. phlei*)-DNA (M-DNA), M-DNA preserved and complexed on *M. phlei* cell wall (MCC) and a chemotherapeutic agent, wherein the M-DNA and the MCC are effective for treating cancer and for potentiating the antineoplastic effect of the chemotherapeutic agent on the cancer.

BACKGROUND OF THE INVENTION

Cancer is an aberrant net accumulation of atypical cells, which results from an excess of proliferation, an insufficiency of cell death, or a combination of the two.

Proliferation is the culmination of a cell's progression through the cell cycle and is characterized by replication of total cellular DNA and the division of one cell into two cells. For cell division, mammalian cells pass through an organized series of controlled events, referred to as the cell cycle. The initiation of an event during cell cycle progression is dependent on the successful completion of an earlier event. The cell cycle can be divided into 5 major phases. These are Go, $G_1$, S, $G_2$ and M. During the Go phase, cells are quiescent. Most cells in the body, at any one time, are in this stage. During the $G_1$ phase, cells, responding to signals to divide, produce the RNA and the proteins necessary for DNA synthesis. During the S-phase (SE, early S-phase; SM, middle S-phase; and SL, late S-phase) the cells replicate their DNA. At the end of the S phase, each cell contains twice its original DNA content but is still bound by one external cell membrane. During the $G_2$ phase, proteins are elaborated in preparation for cell division. During the mitotic (M) phase, the cell divides into two daughter cells.

Alterations in cell cycle progression occur in all cancers and may result from over-expression of genes, mutation of regulatory genes or abrogation of DNA damage checkpoints, and may modulate the cellular response to treatment with chemotherapeutic agents (Hochhauser D. Anti-cancer Chemotherapeutic Agents 8:903, 1997).

Cell death is effected by immune-mediators that initiate cytolytic processes and that promote apoptosis, and from apoptosis inducers that directly initiate pathways leading to cell death. Apoptosis is an active cellular death process characterized by distinctive morphological changes that include condensation of nuclear chromatin, cell shrinkage, nuclear disintegration, plasma membrane blebbing, and the formation of membrane-bound apoptotic bodies (Wyllie et al. Int. Rev. Cytol. 68:251, 1980). A molecular hallmark of apoptosis is degradation of the cell's nuclear DNA into oligonucleosomal-length fragments as the result of activation of endogenous endonucleases (Wyllie A. Nature 284:555, 1981).

Caspases have been implicated as key enzymes in the execution phase of apoptosis. The caspase family consists of at least fourteen related cysteine aspartane proteases. All the caspases contain a conserved QACXG (where X is R, Q or G) (SEQ ID NO: 1) pentapeptide active-site motif (Cohen G. Biochim. Biophys. Acta 1366:139, 1997). A number of caspases are synthesized as inactive proenzymes, which are activated following cleavage at specific aspartate cleavage sites (Cohen G. Biochim. Biophys. Acta 1366:139, 1997) or as inactive enzymes that require association with regulatory molecules for activation (Stennicke et al. J. Biol. Chem. 274:8359, 1999). Activation of the initiator procaspase activates downstream effector caspases triggering the cell death cascade (Pan et al. J. Biol. Chem. 273:5841, 1998; Earnshaw W. Nature 397:387, 1999).

Most currently used chemotherapeutic agents are nonspecifically cytotoxic. Many of these chemotherapeutic agents have toxic side effects, are debilitating and often compromise the quality of life of the patient. Moreover, alterations in the transport and metabolism of chemotherapeutic agents by the cancer cells result in the development of resistance to the chemotherapeutic agents by the cancer cells.

Therefore, there is a continuing need for novel compositions and methods that induce cell cycle arrest in cancer cells, that inhibit proliferation of cancer cells, that induce apoptosis in cancer cells and that potentiate the antineoplastic effect of chemotherapeutic agents on cancer cells. Moreover, such compositions should be simple and relatively inexpensive to prepare, their activity should remain therapeutically stable over time and they should be effective at dose regimens that are associated with minimal toxicity even upon repeated administration.

SUMMARY OF THE INVENTION

The present invention satisfies these needs by providing a composition and method comprising *Mycobacterium phlei* (*M. phlei*)-DNA (M-DNA), M-DNA preserved and complexed on *M. phlei* cell wall (MCC). a chemotherapeutic agent and a pharmaceutically acceptable carrier, wherein the M-DNA and the MCC induce cell cycle arrest in cancer cells, inhibit proliferation of cancer cells, induce apoptosis in cancer cells and potentiate the antineoplastic effect of the chemotherapeutic agent on cancer cells. Moreover, M-DNA and MCC are simple and relatively inexpensive to prepare, their activity is reproducible among preparations, remains therapeutically stable over time, and is effective at dose regimens that are associated with minimal toxicity even upon repeated administration.

To prepare MCC, *M. phlei* are grown in liquid medium and harvested. The *M. phlei* are disrupted, and the solid components of the disrupted *M. phlei* are collected by centrifugal sedimentation. The solid components are deproteinized, delipidated, and washed. All reagents are selected to enhance conservation of DNA during MCC preparation. M-DNA is prepared from MCC or directly from *M. phlei*. Again, all reagents are selected to enhance conservation of DNA during M-DNA preparation.

A composition comprising M-DNA, MCC, M-DNA+ chemotherapeutic agent or MCC+ chemotherapeutic agent is administered to an animal, including a human, having cancer in an amount effective to treat the cancer in the animal. The unexpected and surprising ability of M-DNA and of MCC to induce cell cycle arrest in cancer cells, to inhibit proliferation of cancer cells, to induce apoptosis in cancer cells and to potentiate the antineoplastic effect of chemotherapeutic agents on cancer cells addresses a long felt unfulfilled need in the medical arts and provides an important benefit for animals, including humans.

Another object of the present invention is to provide a composition and method that induces cell cycle arrest in cancer cells.

Another object of the present invention is to provide a composition and method that inhibits proliferation of cancer cells.

Another object of the present invention to provide a composition and method that potentiates the antineoplastic effect of a chemotherapeutic agent on cancer cells.

Another object of the present invention to provide a composition and method that potentiates the effect of a chemotherapeutic agent on cancer cells by synchronizing the cell cycle of the cancer cells.

Another object of the present invention is to provide a composition and method that potentiates the effect of a chemotherapeutic agent on proliferation of cancer cells.

Another object of the present invention is to provide a composition and method effective to treat cancer in an animal, including a human.

Another object of the present invention is to provide a composition and method that potentiates the antineoplastic effect of a chemotherapeutic agent in treating cancer in an animal, including a human.

Another object of the present invention is to provide a composition and method effective to eliminate cancer in an animal, including a human.

Another object of the present invention is to provide a composition and method that potentiates the antineoplastic effect of a chemotherapeutic agent in eliminating cancer in an animal, including a human.

Another object of the present invention is to provide a composition and method that induces cell cycle arrest in malignant melanoma cells.

Another object of the present invention is to provide a composition and method that inhibits proliferation of malignant melanoma cells.

Another object of the present invention to provide a composition and method that potentiates the antineoplastic effect of a chemotherapeutic agent on malignant melanoma cells.

Another object of the present invention is to provide a composition and method that potentiates the antineoplastic effect of a chemotherapeutic agent on cell cycle arrest in malignant melanoma cells.

Another object of the present invention is to provide a composition and method that potentiates the antineoplastic effect of a chemotherapeutic agent on proliferation of malignant melanoma cells.

Another object of the present invention is to provide a composition and method that induces apopotosis in malignant melanoma cells.

Another object of the present invention is to provide a composition and method that activates caspases in malignant melanoma cells.

Another object of the present invention to provide a composition and method effective to treat malignant melanoma in an animal, including a human.

Another object of the present invention is to provide a composition and method that potentiates the antineoplastic effect of a chemotherapeutic agent in treating malignant melanoma in an animal, including a human.

Another object of the present invention is to provide a composition and method effective to eliminate malignant melanoma in an animal, including a human.

Another object of the present invention is to provide a composition and method that potentiates the antineoplastic effect of a chemotherapeutic agent in eliminating malignant melanoma in an animal, including a human.

Another object of the present invention is to provide a composition and method that potentiates the effect of radiation in treating cancer in an animal, including a human.

Another object of the present invention is to provide a composition and method that potentiates the effect of radiation in eliminating cancer in an animal, including a human.

Another object of the present invention to provide a composition and method that potentiates the effect of radiotherapy on cancer cells by synchronizing the cell cycle of the cancer cells.

Another object of the present invention is to provide a composition that can be prepared in large amounts.

Another object of the present invention is to provide a composition that is relatively inexpensive to prepare.

Another object of the present invention is to provide a composition that has reproducible activity among preparations.

Another object of the present invention is to provide a composition that remains stable over time.

These and other objects, features and advantages of the present invention will become apparent after a review of the following detailed description of the disclosed embodiment and the appended claims.

DETAILED DESCRIPTION OF THE INVENTION

Figure 1:
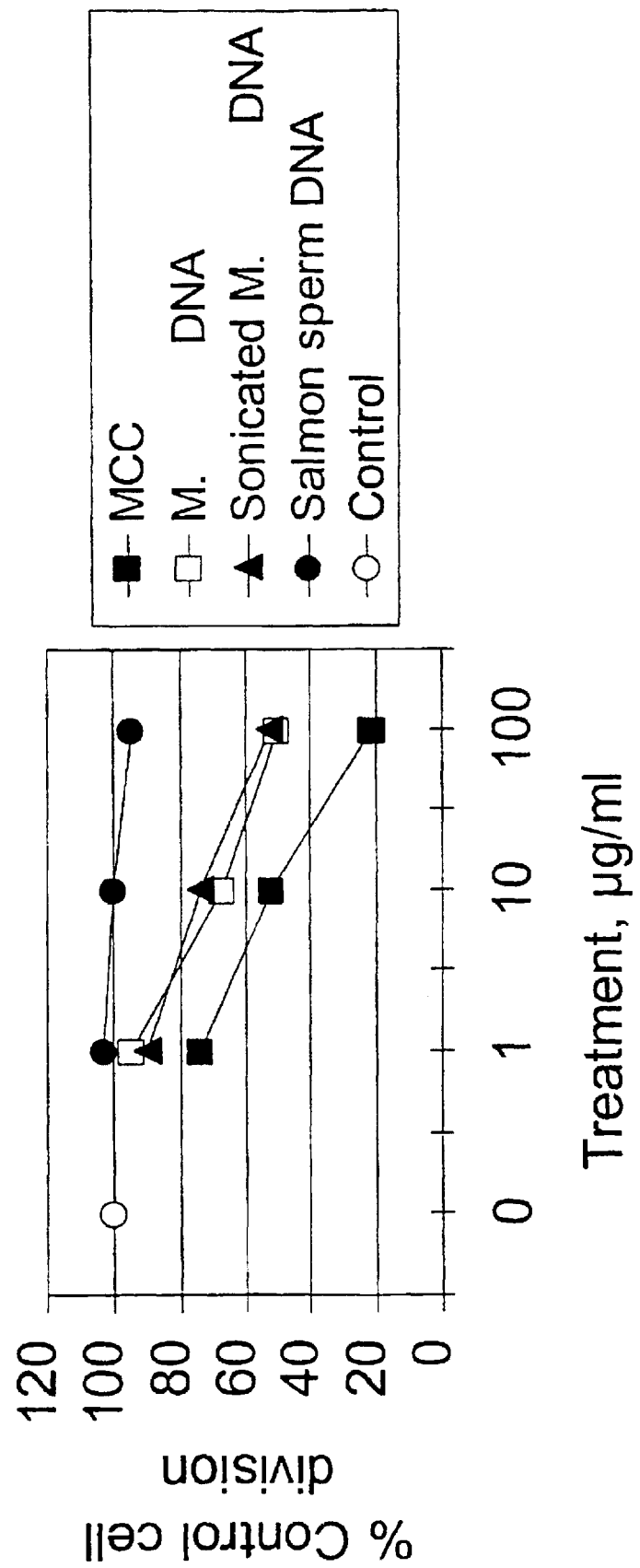
FIG. 1. Inhibition of B-16 melanoma cell division by MCC, M-DNA, sonicated M-DNA and herring sperm DNA.

The present invention is a composition and method comprising *Mycobacterium phlei* (*M. phlei*)-DNA (M-DNA), M-DNA preserved and complexed on *M. phlei* cell wall (MCC), a chemotherapeutic agent and a pharmaceutically acceptable carrier, wherein the M-DNA and the MCC induce cell cycle arrest in cancer cells, inhibit proliferation of cancer cells, induce apoptosis in cancer cells and potentiate the antineoplastic effect of the chemotherapeutic agent on cancer cells. M-DNA and MCC are simple and relatively inexpensive to prepare, their activity is reproducible among preparations, remains therapeutically stable over time, and is effective at dose regimens that are associated with minimal toxicity even upon repeated administration.

As used herein, "M-DNA" includes DNA isolated from *M. phlei* directly and DNA isolated from MCC prepared from *M. phlei*.

As used herein, "MCC" is M-DNA preserved and complexed on deproteinized, delipidated *M. phlei* cell wall.

As used herein, "chemotherapeutic agent" is any agent approved by a regulatory agency of a country or a state government or listed in the U.S. Pharmacopoeia or other generally recognized pharmacopoeia for use in treating cancer in an animal, including a human.

As used herein, "antineoplastic" relates to preventing the development, maturation, proliferation and spread of cancer cells.

As used herein, "potentiates" relates to a degree of synergism that is greater than additive.

As used herein, "synergism" relates to the coordinated action of two or more chemotherapeutic agents.

As used herein, "enhances" relates to the additive action of two or more chemotherapeutic agents.

Methods to increase the therapeutic effectiveness of M-DNA and MCC include, but are not limited to, chemically supplementing or biotechnologically amplifying stimulatory sequences or confirmations of M-DNA and complexing the M-DNA, MCC M-DNA+ chemotherapeutic agent and MCC+ chemotherapeutic agent to natural or synthetic carriers. Optionally, agents including but not limited to, immunological agents and receptor-binding agents can be included in the M-DNA and the MCC.

M-DNA, MCC, M-DNA+ chemotherapeutic agent and MCC+ chemotherapeutic agent are administered in a pharmaceutically acceptable carrier including, but not limited to, a liquid carrier and a solid carrier. Liquid carriers are aqueous carriers, non-aqueous carriers or both and include, but are not limited to, aqueous suspensions, oil emulsions, water in oil emulsions, water-in-oil-in-water emulsions, site-specific emulsions, long-residence emulsions, sticky-emulsions, microemulsions, nanoemulsions and liposomes. Solid carriers are biological carriers, chemical carriers or both and include, but are not limited to, microparticles, nanoparticles, microspheres, nanospheres, minipumps, bacterial cell wall extracts and biodegradable or non-biodegradable natural or synthetic polymers that allow for sustained release of the M-DNA, MCC, M-DNA+ chemotherapeutic agent or MCC+ chemotherapeutic agent. Such polymers can be implanted in the vicinity of where delivery is required. Polymers and their use are described in, for example, Brem et al., J. Neurosurg. 74:441–446 (1991).

Preferred aqueous carriers include, but are not limited to, DNase-free water, DNase-free saline and DNase-free physiologically acceptable buffers. Preferred non-aqueous carriers include, but are not limited to, mineral oil or neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the number of fatty acid carbons is between 12 and 22 and wherein the fatty acids can be saturated or unsaturated. Optionally, charged lipid or phospholipid can be suspended in the neutral oil.

In an example, M-DNA is suspended in DNase-free sterile water and is sonicated at 20% output for 5 minutes (Model W-385 Sonicator, Heat Systems-Ultrasonics Inc). Optionally, the sonicated M-DNA is homogenized by microfluidization at 15,000–30,000 psi for one flow-through (Model M-110Y; Microfluidics, Newton, Mass.) and is transferred to an autoclaved, capped bottle for storage at 4° C.

In an example, DNase free phosphatidylcholine is added to DNase free triglyceride soybean oil at a ratio of 1 gram of phospholipid to 20 ml of triglyceride and is dissolved by gentle heating at 50°–60° C. Several grams of MCC are added to a dry autoclaved container and the phospholipid-triglyceride solution is added at a concentration of 20 ml per 1 gram of MCC. The suspension is incubated at 20° C for 60 min. and is then mixed with DNase-free PBS in the ratio of 20 ml MCC suspension per liter of DNase-free PBS. The mixture is sonicated at 20% output for 5 minutes (Model W-385 Sonicator, Heat Systems-Ultrasonics Inc.). Optionally, the sonicated MCC mixture is homogenized by microfluidization at 15,000–30,000 psi for one flow-through (Model M-110Y; Microfluidics) and is transferred to an autoclaved, capped bottle for storage at 4° C.

A chemotherapeutic agent can be added to M-DNA or to MCC before, during or after sonication or microfluidization or before or after storage. Moreover, other methods known to those skilled in the art for preparing deoxyribonucleic acids, bacterial cell wall extracts and chemotherapeutic agents for administration to an animal, including a human can be used.

Further, M-DNA, MCC, M-DNA+ chemotherapeutic agent and MCC+ chemotherapeutic agent can be used with any one, all, or any combination of excipients regardless of the carrier used to present the composition to the responding cells. These include, but are not limited to, anti-oxidants, buffers and bacteriostats, and may include suspending agents, thickening agents and stabilizing agents. Stabilizing agents include, but are not limited to, non-ionic and ionic polymers such as, for example, polyoxyethylenesorbitan monooleate (Tween) or hyaluronic acid.

M-DNA, MCC, M-DNA+ chemotherapeutic agent and MCC+ chemotherapeutic agent are administered to an animal having cancer in an amount effective to induce cell cycle arrest in cancer cells, to inhibit proliferation of cancer cells, to induce apoptosis in cancer cells and to potentiate the antineoplastic effect of the chemotherapeutic agent on cancer cells. The chemotherapeutic agent can be administered before, at the same time as, or after administration of the M-DNA or the MCC. The chemotherapeutic agent used and the amount of M-DNA, MCC and chemotherapeutic agent administered per dose, the number of doses and the dose schedule will depend on the type of cancer, the severity of the cancer, the location of the cancer and other clinical factors such as the size, weight and physical condition of the recipient and the route of administration and can be determined by the medical practitioner using standard clinical techniques and without undue experimentation. In addition, in vitro assays may optionally be employed to help identify optimal ranges for M-DNA, MCC, M-DNA+ chemotherapeutic agent and MCC+ chemotherapeutic agent administration.

Preferably, the amount of M-DNA administered is from about 0.00001 to 500 mg/kg per dose, more preferably from about 0.0001 to 100 mg/kg per dose, and most preferably from about 0.001 to 40 mg/kg per dose. Preferably, the amount of MCC administered is from about 0.00001 to 500 mg/kg per dose, more preferably from about 0.0001 to 100 mg/kg per dose, and most preferably from about 0.001 to 40 mg/kg per dose. Preferably, the M-DNA content of the MCC is between about 0.001 and 90 mg/100 mg dry MCC, more preferably between about 0.01 and 40 mg/100 mg dry MCC, and most preferably between about 0.1 and 30 mg/100 mg dry MCC. The protein content of the MCC should be less than about 20 mg/100 mg dry MCC and the extractable M-DNA should be at least about 4.5% of the dry weight of MCC.

Chemotherapeutic agents include, but are not limited to, DNA-alkylating agents, anti-tumor antibiotic agents, antimetabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metaloproteinase inhibitors, antisense nucleic acids, triple-helix DNAs, nucleic acids aptamers, and molecular biologically modified viral, bacterial and extotoxic agents.

DNA-alkylating agents include, but are not limited to, nitrosureas, heavy metal agents and cross-linking agents; antitumor antibiotic agents include, but are not limited to, mitomycin-C; antimetabolic agents include, but are not limited to, 5-fluorouracil and methotrexate; topoisomerase inhibiting agents include, but are not limited to, CPT-11; tubulin stabilizing agents include, but are not limited to, taxol; tubulin destabilizing agents include, but are not limited to, vincristine and vinblasitne; and, hormone antagonist agents include, but are not limited to, tamoxifen.

Preferably, the amount of chemotherapeutic agent administered per dose is from about 0.0001 to 1000 mg/m$^2$ or from about 0.0001 to 1000 mg/kg, more preferably from about 0.5 to 70 mg/m$^2$ or about 0.5 to 70 mg/kg and most preferably from about 1 to 50 mg/m$^2$ or about 1 to 50 mg/kg.

Routes for administration of the composition of the present invention include, but are not limited to, oral, topical, subcutaneous, transdermal, subdermal, intramuscular intra-peritoneal, intra-articular, intra-vesical, intra-arterial, intra-venous, intra-dermal, intra-cranial, intra-lesional, intra-tumoral, intra-ocular, intra-pulmonary, intra-spinal, placement within cavities of the body, nasal inhalation, pulmonary inhalation, impression into skin and electrocorporation. Depending on the route of administration, the volume per dose is preferably about 0.001 to 500 ml per dose, more preferably about 0.01 to 100 ml per dose and most preferably about 0.1 to 50 ml per dose.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1
Preparation of M-DNA and MCC from *M. phlei*

M-DNA and MCC were prepared from *M. phlei* (strain 110) as described in International Patent Application No. PCT/CA98/00744, which is included by reference herein. All reagents were selected to enhance conservation of the DNA. Unless stated otherwise, M-DNA and MCC were resuspended in DNase-free water or in a pharmaceutically acceptable DNase-free buffer and sonicated at 20% output for 5 minutes (Model W-385 Sonicator, heat systems-Ultrasonics, Inc). M-DNA and MCC did not contain endotoxins as determined using a Limulus amebocyte lysate QCL-1000 kit (BioWhittaker, Walkersville, Md.).

For DNase treatment, M-DNA and MCC were digested with 1 International Unit of RNase-free DNase I (Life Technologies) for 1 hour at 25° C. in 20 mM Tris HCl, pH 8.4, 2 mM MgCl$_2$ and 50 mM KCl. DNase I was activated by the addition EDTA to a final concentration of 25 mM and heating for 10 min at 65° C. DNase I digests both double stranded and single stranded DNA and provides almost total degradation of the DNA.

EXAMPLE 2
Preparation of Mycobacterial DNA (B-DNA) and of Mycobacterial DNA Preserved and Complexed on Mycobacterial Cell Wall (BCC) from Species Other than *M. phlei*

BCC and B-DNA were prepared from mycobacterial species including, but not limited to, *M. vaccae, M. chelonei, M. smegmatis, M. terrae, M. duvalii, M. tubeculosis, M. bovis* BCG, *M. avium, M. Szulgai, M. scrofulaceum, M. xenopi, M. kansaii, M. gastr, M. fortuitous* and *M. asiaticum* as in Example 1.

EXAMPLE 3
Cells and Reagents

Human Jurkat T cell leukemia cells (Jurkat), human promyelocytic HL60 leukemia cells (HL-60), mitoxantrone resistant human promyelocytic HL-60MX1 leukemia cells (HL-60MX1), murine EL-4 lymphoma cells (EL-4) and murine B-16 melanoma cells were obtained from the American Type Tissue Culture Collection (ATCC Rockville, Md., USA) and were grown in medium recommended by the ATCC. Unless stated otherwise, cells were seeded in 6 well flat-bottom tissue culture plates at concentrations of $5 \times 10^3$ to $1 \times 10^6$ cells/ml and were maintained at 37° C. for 24 to 72 hours.

Mitomycin-C, 5-fluorouracil, cisplatin, methotrexate and herring sperm-DNA were obtained from Sigma Aldrich Canada (Oakville, Ontario, Canada)

EXAMPLE 4
Cell Cycle Analysis

Cell cycle stage was determined using a CYCLETEST™ PLUS DNA commercial kit (Becton Dickinson, San Jose, Calif., USA). Briefly, nuclei from treated cells were obtained by dissolving the cell membrane in a nonionic detergent, eliminating the cell cytoskeleton and nuclear proteins with trypsin, digesting the cellular RNA with RNase, and stabilizing the nuclear chromatin with spermine. Propidium iodide was added to the cell nuclei and their fluorescence was analyzed in a flow cytometer equipped with electronic doublet discrimination capability (FACSCalibur, Becton Dickinson). Accumulation of cells in G0/G$_1$, S (SE, SM, SL) or G$_2$/M phases of the cell cycle was analyzed using MODFIT LT software (Verity Software House Inc., Topsham, Mass., USA). Results are expressed as percentage of cells in each phase of the cell cycle.

EXAMPLE 5
Synchronization of Cell Populations with Methotrexate

To synchronize cell populations, exponentially growing cells were incubated in tissue culture medium containing 0.04 to 0.16 μM methotrexate (MTX) for 20 hours. The MTX medium was removed, cells were washed extensively with phosphate buffered saline (PBS), fresh medium was added, incubation was continued for 8 hours and cell cycle analysis was performed as in Example 4.

EXAMPLE 6
Induction of Cell Cycle Arrest in Synchronously Dividing Cancer Cells by MCC Exponentially growing Jurkat, HL-60, HL-60MX1 and EL-4 cells, at $1 \times 10^6$ cells/ml, and B-16 cells, at $3 \times 10^5$ cells/ml, were prepared for analysis as in Example 5 with 0, 10 and 100 μg/ml of MCC in the MTX medium.

Table 1 shows that MCC, at both 10 and 100 μg/ml, induced arrest at the SL+G$_2$M phase of the cell cycle in synchronously dividing Jurkat, HL-60, HL-60MX1, EL-4 and B-16 cancer cells. Accumulation of cells in the SL+G$_2$M phase was accompanied by a reduction of cells in the G0/G$_1$+SE phase or in the G0/G$_1$+SE and SM phases of the cell cycle.

TABLE 1

Induction of cell cycle arrest in synchronously dividing cancer cells by MCC

PERCENTAGE OF CELLS IN EACH PHASE

| Cells | MTX alone | | | MTX + MCC 10 μg/ml | | | MTX + MCC 100 μg/ml | | |
|---|---|---|---|---|---|---|---|---|---|
| | $G_0G_1$ + SE | SM | SL + $G_2$M | $G_0G_1$ + SE | SM | SL + $G_2$M | $G_0G_1$ + SE | SM | SL + $G_2$M |
| Jukat[a] | 44.6 | 25.3 | 30.1 | 35.6 | 17.6 | 43.8 | 29.4 | 21.0 | 49.6 |
| EL-4[b] | 18.3 | 18.4 | 63.3 | 7.5 | 7.3 | 85.2 | 6.6 | 7.4 | 86.0 |
| B-16 | 48.3 | 5.4 | 46.3 | 38.3 | 5.9 | 55.8 | 31.2 | 8.1 | 60.7 |
| HL-60[c] | 50.3 | 24.2 | 25.5 | 48.1 | 24.2 | 27.7 | 35.3 | 24.7 | 40.0 |
| HL-60 MX1[c] | 46.1 | 35.5 | 18.4 | 41.4 | 30.7 | 27.9 | 38.0 | 25.1 | 36.9 |

[a]0.08 μM,

[b]0.16 uM or

[c]0.04 μM

These data demonstrate that MCC induced arrest in synchronously dividing cancer cells, including HL-60MX1 cancer cells, which display atypical multi-chemotherapeutic agent resistance, altered topoisomerase II catalytic activity and reduced levels of topoisomerase II alpha and beta proteins (Harker et al. Cancer Res 49:4542–4549, 1989).

EXAMPLE 7
Induction of Cell Cycle Arrest in Synchronously Dividing Jurkat Leukemia Cells by MCC and DNase I-treated MCC Exponentially growing Jurkat leukemia cells, at 1×10$^6$ cells/ml, were prepared for analysis as in Example 5 with 0 and 10 μg/ml of MCC and 10 μg/ml DNase I-treated MCC in the MTX medium.

Table 2 shows that MCC induced arrest at the SL+$G_2$M phase of the cell cycle in synchronized Jurkat cells. Accumulation of cells in the SL+$G_2$M phase was accompanied by a reduction of cells in the GO/$G_1$+SE phase or in the GO/$G_1$+SE and SM phases of the cell cycle. Table 2 also shows that DNase I-treated MCC did not induce cell cycle arrest in synchronously dividing Jurkat cells.

MCC is M-DNA preserved and complexed on *M. phlei* cell wall and DNase I digests the M-DNA of MCC. Therefore, that DNase I treated MCC did not induce arrest in synchronously dividing Jurkat leukemia cells demonstrates the importance of M-DNA for MCC induction of cell cycle arrest in dividing cancer cells.

EXAMPLE 8
Induction of Cell Cycle Arrest in Cancer Cells by MCC

Exponentially growing Jurkat, HL-60, HL-60MX1 and EL-4 cells, at 1×106 cells/ml, and B-16 cells, at 3×105 cells/ml, were prepared for analysis as in Example 5 in the absence of MTX and in the presence of 0, 10 and 100 μg/ml of MCC Table 3 shows that MCC, at both 10 and 100 μg/ml, induced arrest at the SL+$G_2$M phase of the cell cycle in asynchronously dividing Jurkat, HL-60, HL-60MX1, EL-4 and B-16 cancer cells. Accumulation of cells in the SL+$G_2$M phase was accompanied by a reduction of cells in the GO/$G_1$+SE phase or in the GO/$G_1$+SE and SM phases of the cell cycle.

TABLE 2

Induction of cell cycle arrest in synchronously dividing Jurkat Cells by MCC and by DNase I treated MCC

PERCENTAGE OF CELLS IN EACH PHASE

| Cells | MTX[a] + MCC 0 μg/ml | | | MTX + MCC 10 μg/ml | | | MTX + MCC + Dnase I 10 μg/ml | | |
|---|---|---|---|---|---|---|---|---|---|
| | $G_0G_1$ + SE | SM | SL + $G_2$M | $G_0G_1$ + SE | SM | SL + $G_2$M | $G_0G_1$ + SE | SM | SL + $G_2$M |
| Jurkat | 43.0 | 25.6 | 31.4 | 34.9 | 11.4 | 53.7 | 36.7 | 26.0 | 37.3 |

[a]MTX = 0.08 μM

TABLE 3

Induction of cell cycle arrest in asynchronously dividing cancer cells by MCC

PERCENTAGE OF CELLS IN EACH PHASE

| | MCC 0 µg/ml | | | MCC 10 µg/ml | | | MCC 100 µg/ml | | |
|---|---|---|---|---|---|---|---|---|---|
| Cells | $G_0G_1$ + SE | SM | SL + $G_2$M | $G_0G_1$ + SE | SM | SL + $G_2$M | $G_0G_1$ + SE | SM | SL + $G_2$M |
| Jukat | 47.2 | 10.7 | 42.1 | 31.8 | 11.5 | 56.7 | 34.1 | 11.9 | 54.0 |
| EL-4 | 55.6 | 15.8 | 28.6 | 47.2 | 14.8 | 38.0 | 44.3 | 12.8 | 42.9 |
| B-16 | 64.2 | 9.4 | 26.4 | 65.8 | 6.6 | 27.6 | 61.9 | 7.3 | 30.8 |
| HL-60 | 64.0 | 8.6 | 27.4 | 54.8 | 9.8 | 35.4 | 49.5 | 7.8 | 42.7 |
| HL60 MX1 | 56.4 | 11.3 | 32.3 | 45.3 | 8.0 | 46.7 | 43.3 | 9.3 | 47.4 |

MCC induced arrest in asynchronously dividing cancer cells, including in HL-60MX1 cells, which display an a typical multi-chemotherapeutic agent resistance, altered topoisomerase II catalytic activity and reduced levels of topoisomerase II alpha and beta proteins (Harker et al. Cancer Res 49:4542–4549, 1989).

EXAMPLE 9
Induction of Cell Cycle Arrest in Jurkat Leukemia Cells by M-DNA, MCC and DNase I-Treated MCC Exponentially growing Jurkat leukemia cells, at $1 \times 10^6$ cells/ml, were prepared for analysis as in Example 5 in the absence of MTX and in the presence of 200 µg/ml M-DNA, 10 µg/ml MCC and 10 µg/ml of DNase I-treated MCC.

Table 4 shows that M-DNA and MCC both induced arrest at the SL+$G_2$M phase of the cell cycle in asynchronously dividing Jurkat cells. Accumulation of cells in SL+$G_2$M phase was accompanied by a reduction of cells in GO/$G_1$+ SE and SM phases of the cell cycle. Table 3 also shows that, after DNase I treatment, MCC induced less cell cycle arrest in asynchronously dividing Jurkat cells.

TABLE 4

Induction of cell cycle arrest in asynchronously dividing Jurkat leukemia cells by M-DNA, MCC and DNase I treated MCC

PERCENTAGE OF CELLS IN EACH PHASE

| | No Treatment | | | M-DNA 200 µg/ml | | |
|---|---|---|---|---|---|---|
| Cells | $G_0G_1$ + SE | SM | SL + $G_2$M | $G_0G_1$ + SE | SM | SL + $G_2$M |
| Jurkat | 35.2 | 9.1 | 55.7 | 20.2 | 4.0 | 75.8 |

| | MCC 10 µg/ml | | | MCC + Dnase I 10 µg/ml | | |
|---|---|---|---|---|---|---|
| Cells | $G_0G_1$ + SE | SM | SL + $G_2$M | $G_0G_1$ + SE | SM | SL + $G_2$M |
| Jurkat | 22.9 | 4.9 | 72.2 | 32.1 | 7.3 | 60.0 |

M-DNA and MCC induced cell cycle arrest in asynchronously dividing Jurkat cells MCC is M-DNA preserved and complexed on *M. phlei* cell wall and DNase I digests the M-DNA of MCC. Therefore, that DNase I treated MCC induced less arrest in asynchronously dividing Jurkat cells again demonstrates the importance of M-DNA for MCC induction of cell cycle arrest in dividing cancer cells.

EXAMPLE 10
Inhibition of B-16 Melanoma Cell Proliferation by MCC, M-DNA, Sonicated M-DNA and Herring Sperm-DNA Exponentially growing B-16 melanoma cells, at $3 \times 10^5$ cells/ml, were prepared for analysis as in Example 5 in the absence of MTX and in the presence 1 to 100 µg/ml MCC, M-DNA or M-DNA sonicated for 20 min on ice in a Model W-38 ultrasonic processor (HeatSystems-Ultrasonics, Inc.) to reduce oligonucleotide length, and herring sperm-DNA.

Figure 6:
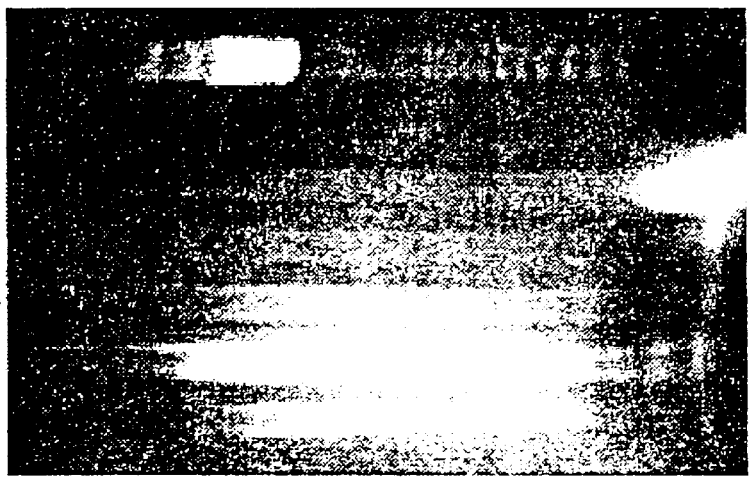
FIG. 6. Induction of apoptosis in B-16 melanoma cells by MCC and M-DNA.

As shown in FIG. 6, at 1 µg/ml, MCC inhibited proliferation about 25%, M-DNA about 5%, sonicated M-DNA about 10% and herring sperm-DNA 0%. At 10 µg/ml, MCC inhibited proliferation about 50%, M-DNA about 30%, sonicated M-DNA about 25% and herring sperm-DNA 0%. At 100 µg/ml, MMC inhibited proliferation about 80%, M-DNA and sonicated M-DNA about 50% and herring sperm-DNA about 5%.

MCC, M-DNA and sonicated M-DNA each inhibited proliferation of asynchronously dividing B-16 melanoma cells, whereas herring sperm-DNA did not inhibit proliferation of asynchronously dividing B-16 melanoma cells.

EXAMPLE 11
Inhibition of B-16 Melanoma Cell Proliferation by Chemotherapeutic Agents± MCC Malignant melanoma is among the most chemotherapy-refractory cancers and many chemotherapeutic agents do not appear to modify the prognosis of this disease. Melanoma derived cells lines also demonstrate significant resistance to most chemotherapeutic agents, suggesting the presence of intrinsic cellular resistance. This resistance may be mediated by mechanisms including, but not limited to, P-glycoprotein, the glutathione/glutathione S-transferase system multi-chemotherapeutic agent resistance-associated protein, mutated N-Ras, Bcl-2 and p53 oncogenes and topoisomerase II enzyme (Serrone et al. Melanoma Res. 9:51, 1999).

B-16 melanoma cells, at $3 \times 10^5$ cells/ml, were incubated for 72 h with the chemotherapeutic agents mitomycin-C, 5-fluorouracil and cisplatin in the absence and in the presence of MCC. Cell proliferation was determined using dimethylthiazol-diphenyltetrazolium bromide (MTT) reduction (Mosman et al. Journal of Immunological Methods 65:55–63, 1983). After 72 h, 20 µl of MTT in culture medium was added to each well and incubated for 3 h. Medium was then aspirated from each well, 100 µl of acidified isopropyl alcohol was added to each sample and reduced MTT was solubilized by mixing. The absorbency of the reaction product was determined using an ELISA microplate reader at a wavelength of 570 nm.

B-16 melanoma cells were incubated with 0.01 to 100 µg/ml of mitomycin-C, with 1 to 100 µg/ml of MCC and with 0.01 to 10 µg/ml of mitomycin-C+1 µg/ml MCC.

Mitomycin-C is an anti-tumor produced by Streptomyces caespitosus, which cross-links DNA, depolymerizes DNA and forms free radicals.

Figure 2:
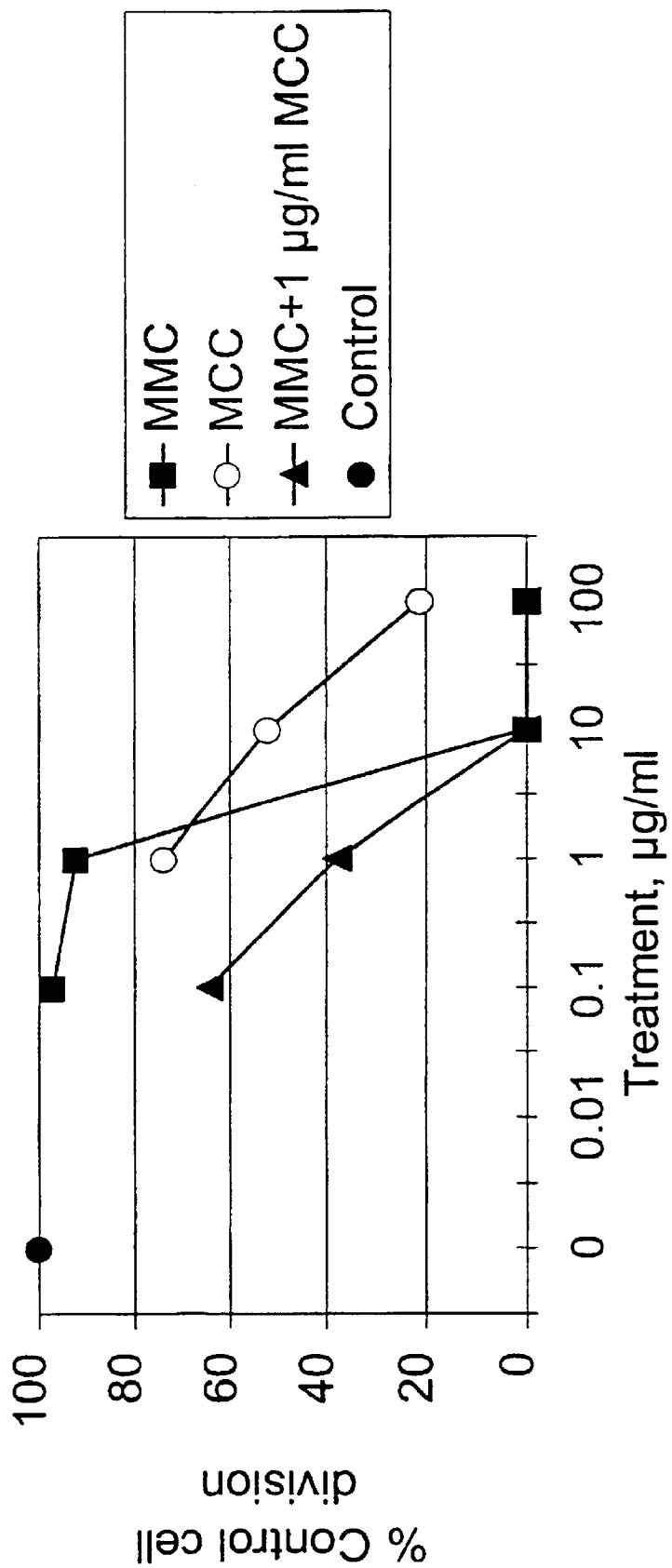
FIG. 2. Inhibition of B-16 melanoma cell division by mitomycin-C, MCC and mitomycin-C+ MCC.

FIG. 2 shows that, with B-16 cells, 0.1 µg/ml mitomycin-C inhibited proliferation about 5%, 1 µg/ml about 10%, and 10 and 100 µg/ml 100%, whereas 1 µg/ml MCC inhibited proliferation about 25%, 10 µg/ml about 50% and 100 µg/ml about 80%. FIG. 2 also shows that, in the present of 1 µg/ml MCC 0.1 µg/ml mitomycin-C inhibited proliferation about 40% 1 µg/ml about 65% and 100 µg/ml 100%. These data show that MCC potentiates the antineoplastic effect of mitomycin-C on proliferating cancer cells.

B-16 melanoma cells were incubated with 0.01 to 100 µg/ml of 5-fluorouracil, with 1 to 100 µg/ml MCC and with 0.01 to 10 µg/ml of 5-fluorouracil+1 µg/ml MCC 5-fluorouracil is an antimetabolize, which interferes with DNA and RNA synthesis.

Figure 3:
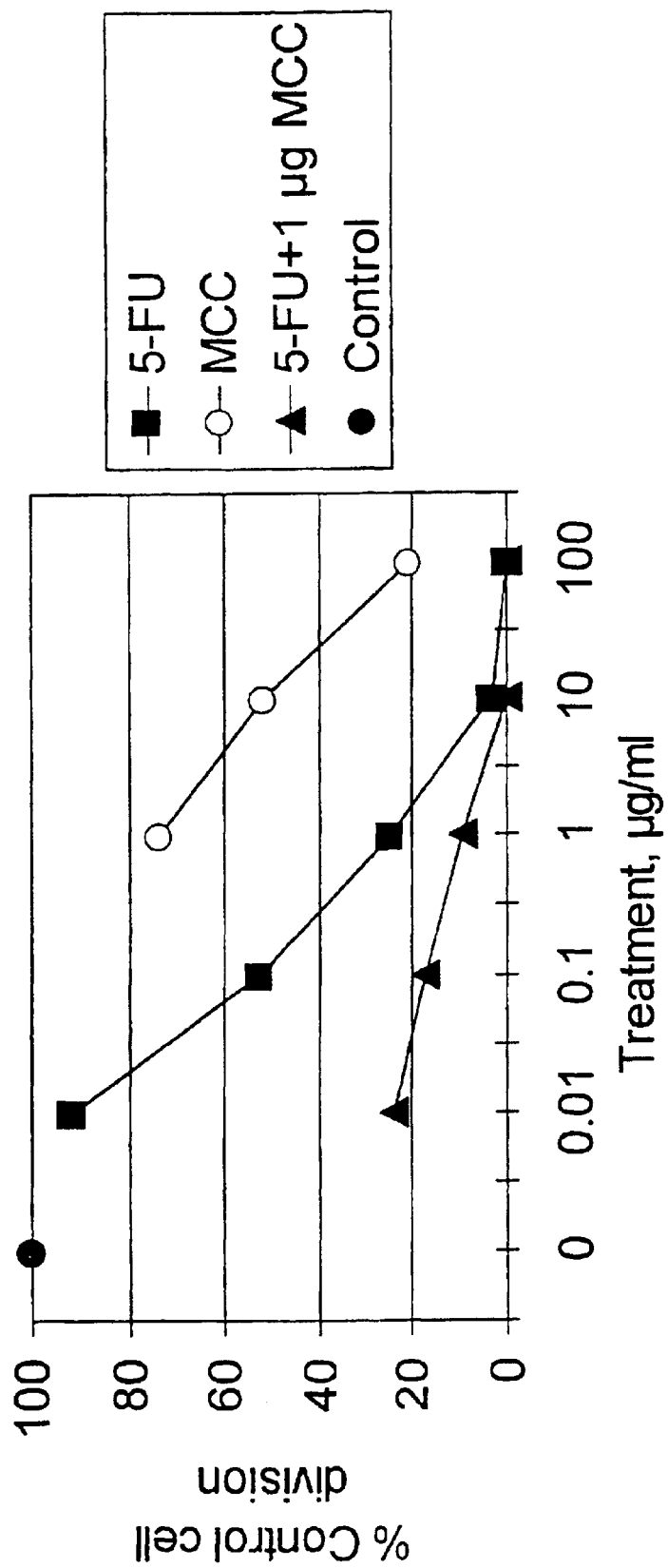
FIG. 3. Inhibition of B-16 melanoma cell division by 5-fluorouracil, MCC and 5-fluorouracil+ MCC.

FIG. 3 shows that, with B-16 cells, 0.01 µg/ml 5-fluorouracil inhibited proliferation about 8%, 0.1 µg/ml about 50%, 1 µg/ml about 90%, and 10 and 100 µg/ml 100%, whereas 1 µg/ml MCC inhibited proliferation about 25%, 10 µg/ml about 50% and 100 µg/ml about 80%. FIG. 3 also shows that, in the presence of 1 µg/ml MCC, 0.01 µg/ml 5-fluorouracil inhibited proliferation about 75%, 0.1 µg/ml about 85%, 1 µg/ml about 90% and 10 µg/ml 100%. These data show MCC potentiates the antineoplastic effect of 5-fluorouracil on proliferating cancer cells.

B-16 melanoma cells were incubated with 0.01 to 100 µg/ml of cisplatin, with 1 to 100 µg/ml of MCC and with 0.01 to 10 µg/ml of cisplatin+1 µg/ml MCC. Cisplatin is an alkylating agent that cross-links DNA and inhibits DNA precursors.

Figure 4:
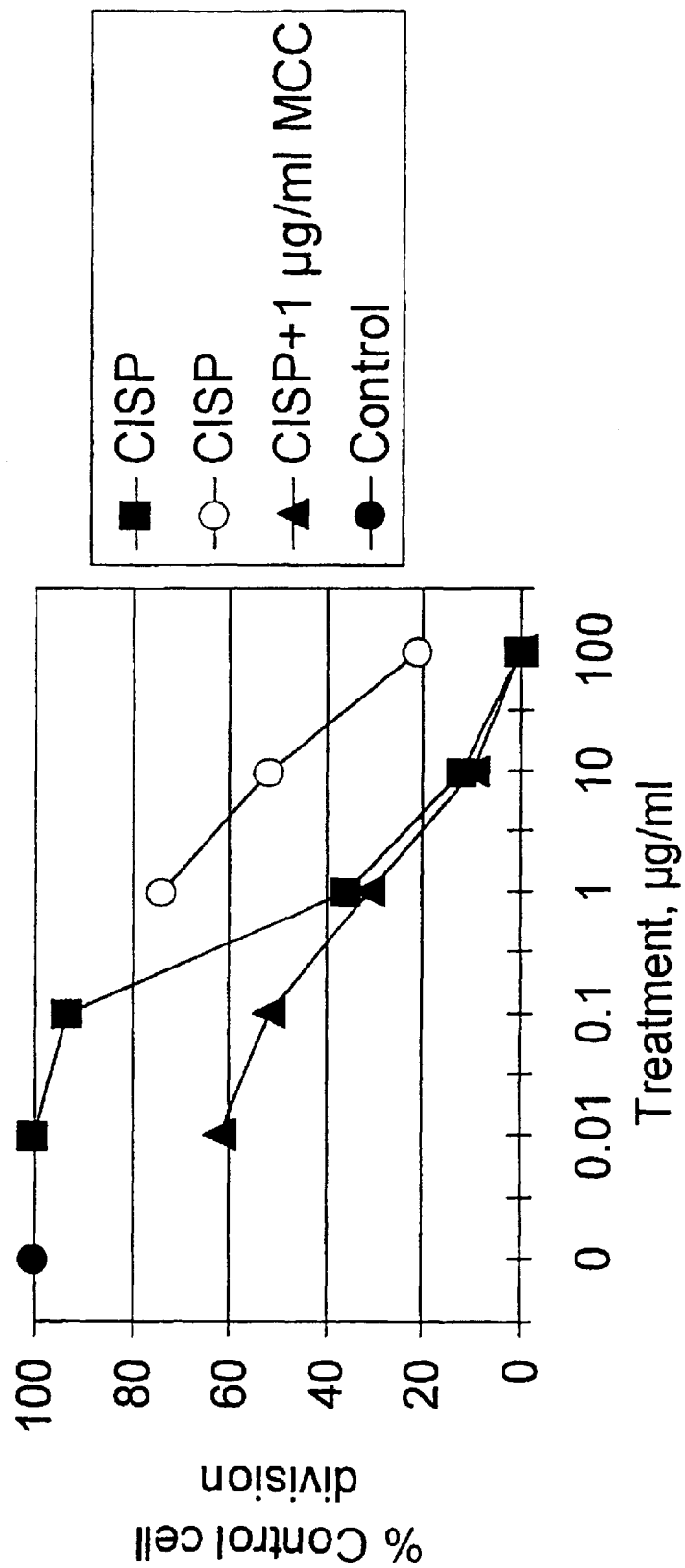
FIG. 4. Inhibition of B-16 melanoma cell division by cisplatin, MCC and cisplatin+ MCC.
Figure 5A:
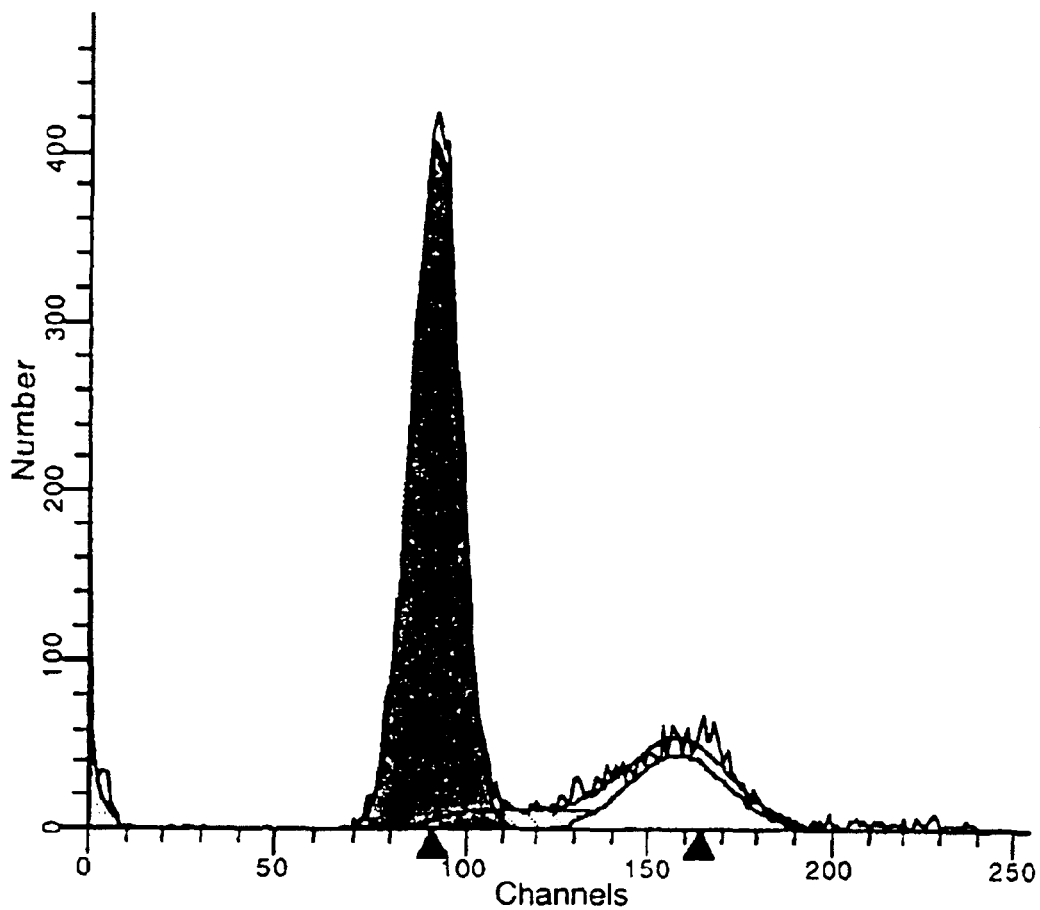
FIG. 5. S-phase assessment of B-16 melanoma cells (A) and S-phase assessment of B-16 melanoma cells after treatment with MCC (B).
Figure 5B:
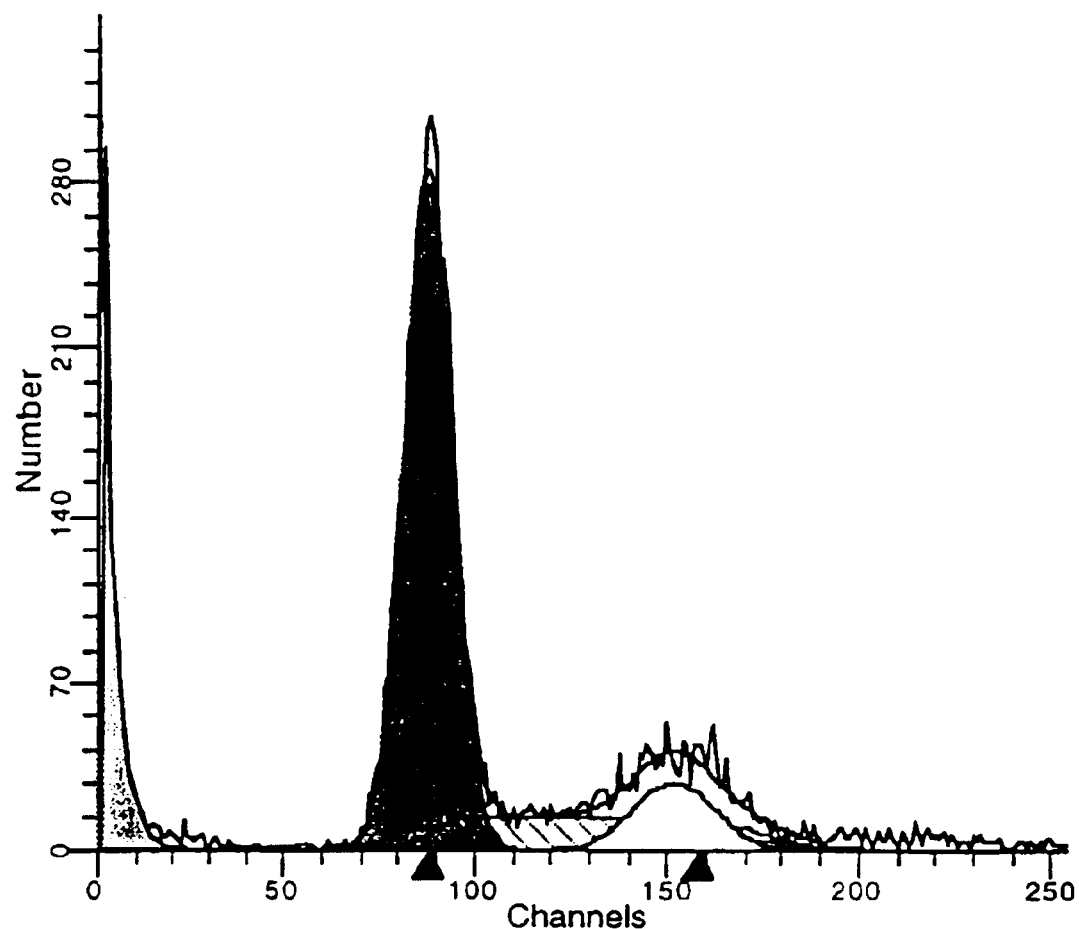

FIG. 4 shows that, with B-16 cells, 0.01 µg/ml cisplatin inhibited proliferation 0%, 0.1 µg/ml about 8%, 1 µg/ml about 62%, 10 µg/ml about 90% and 100 µg/ml 100%, whereas 1 µg/ml MCC inhibited proliferation about 25%, 10 µg/ml about 50% and 100 µg/ml about 80%. FIG. 4 also shows that, in the presence of 1 µg/ml MCC. 0.01 µg/ml cisplatin inhibited proliferation about 40%, 0.1 µg/ml about 50%, 1 µg/ml about 70% and 10 µg/ml about 90%. These data show that MCC enhances the antineoplastic effect of cisplatin on proliferating cancer cells.

Table 5 shows the concentrations of mitomycin-C, 5-fluorouracil, and cisplatin required for 50% inhibition B-16 melanoma cell division in the absence and in the presence of 1 µg/ml MCC.

TABLE 5

Concentration of mitomycin-C, 5-fluorouracil and cisplatin required for 50% inhibition of B-16 melanoma cell proliferation in the absence and in the presence of 1 µg/ml MCC

| Treatment | $IC_{50}$*, µg/ml | |
|---|---|---|
| | Drug Alone | Drug + MCC at 1 µg/ml |
| MCC | 10 | Not applicable |
| Cisplatin | 0.6 | 0.16 |
| 5-Fluorouracil | 0.12 | 0.005 |
| Mitomycin-C | 2.2 | 0.12 |

*concentration for 50% inhibition

Table 5 shows the dose dependent inhibition of B-16 cell melanoma proliferation by MCC at 10 to 100 µg/ml ($IC_{50}$= 10 µg/ml) and by mitomycin-C 5-fluorouracil and cisplatin at 0.1 to 10 µg/ml ($IC_{50}$=2.2, 0.12 and 0.6 µg/ml respectively). Table 5 also shows that 1 µg/ml MCC potentiated mitomycin-C ($IC_{50}$=0.12 µg/ml) and 5-fluorouracil ($IC_{50}$=0.005 µg/ml) inhibition of B-16 melanoma cell proliferation and that 1 µg/ml MCC enhanced cisplatin ($IC_{50}$= 0.16 µg/ml) inhibition of B-16 melanoma proliferation These data show that MCC not only inhibits cancer cell proliferation, but also potentiates the antineoplastic effects of mitomycin-C and 5-fluorouracil on cancer cell proliferation and enhances the antineoplastic effect of cisplatin on cancer cell proliferation.

EXAMPLE 12
Induction of Apoptosis in B-16 Melanoma Cells by MCC and M-DNA

Fragmentation of cellular DNA into nucleosome-sized fragments is characteristic of cells undergoing apoptosis (Newell et al. Nature 357:286–289, 1990). To assess DNA fragmentation, B-16 cells were lysed with 0.5 ml of hypotonic lysing buffer (10 mM Tris buffer, 1 mM EDTA, 0.2% t-octylphenoxypolyethoxyethanol (Triton X-100), pH 7.5). The lysates were centrifuged at 13,000 g for 10 min and the supernatants, containing fragmented DNA, were precipitated overnight at –20° C. in 50% isopropanol and 0.5 M NaCl. The precipitates were collected by centrifugation and were analyzed by electrophoresis in 0.7% agarose gels for 3 h at 100V.

B-16 melanoma cells, at $3\times10^5$ cells/ml, were incubated for 72 h with 1 µg/ml M-DNA (FIG. 6, lane 1) and with 100 (lane 2), 10 (lane 3) and 1 µg/ml MCC (lane 4). M-DNA and MCC treated B-16 melanoma cells showed significant DNA fragmentation, whereas untreated B-16 melanoma cells (FIG. 6, and lane 5) showed no DNA fragmentation. A 123-bp DNA ladder (Gibco Life Science) was used to determine the molecular weight of the nucleosome-sized DNA fragments (FIG. 6, lane L). These data show M-DNA and MCC induce apoptosis in B-16 melanoma cells.

EXAMPLE 13
Activation of Caspase-1 in B-16 Melanoma Cells by MCC

Interleukin-1-converting enzyme (ICE/caspase-1) is a cysteine protease involved in the sequential activation of the caspase cascade required for apoptosis. ICE/caspase-1 is rapidly and transiently activated by various pro-apoptotic stimuli. To determine if MCC can directly activate the ICE/caspase-1, the effect of MCC on ICE/caspase-1 activity was assayed in B-16 melanoma cells.

B-16 melanoma cells, at $3\times10^5$ cells/ml, were plated in 6 well tissue culture plates in a volume of 1 ml and were incubated for 3 h with 1 to 100 µg/ml MCC. The cells were washed, lysed in 50 mM HEPES, pH 7.4, 100 mM NaCl, 0.1% 3-[3-cholamidopropyl)dimethylammonio]-1-propane-sulfonate (CHAPS), 10 mM DTT, 1 mM EDTA and 10% glycerol and centrifuged at 11,000 g for 10 minutes. ICE/caspase-1 activity in the supernatant was determined using the fluorogenic synthetic substrate Z-tyr-val-ala-asp [OMe]-7-amino-4-methylcoumarin [Calbiochem #6 88225]. Fluorescence was determined at an excitation wavelength of 400 nm and an emission wavelength of 505 nm.

Figure 7:
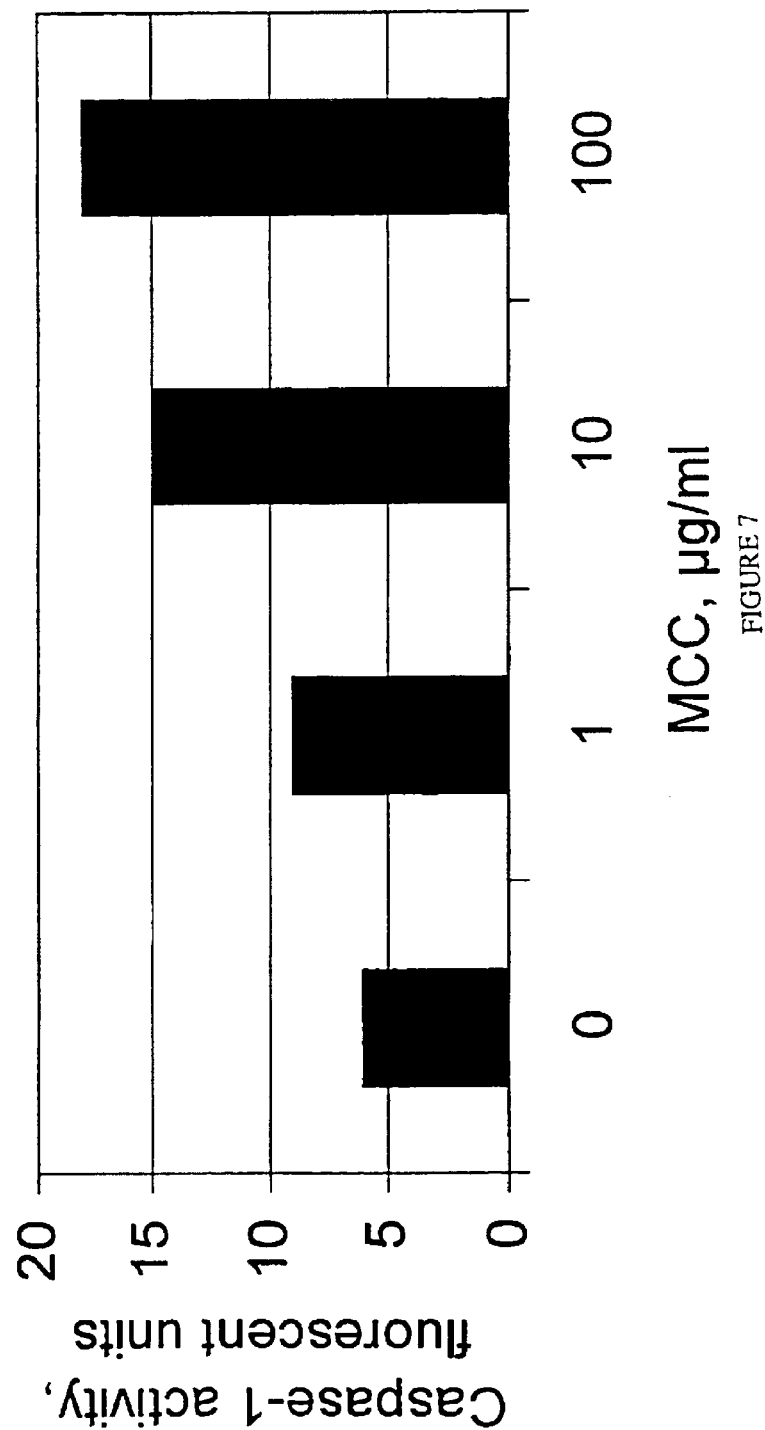
FIG. 7. Induction of caspase-1 activity in B-16 melanoma cells by MCC.

As shown in FIG. 7, incubation of B-16 melanoma cells with MCC resulted in a significant dose-dependent increase in ICE/caspase-1 activity, whereas incubation of B-16 melanoma cells without MCC resulted in no change in ICE/caspase-1 activity.

EXAMPLE 14
Cytotoxic Effects of MCC on Malignant Melanoma Cells

Cell cytotoxicity is characterized by the loss of plasma membrane integrity and release of cytoplasmic enzymes such as, but not limited to, LDH (Phillips et al. Vaccine 14:898–904).

To assess the cytotoxicity of MCC, B-16 melanoma cells were incubated for 48 h with 100 µg/ml MCC or with lysing buffer (10 mM Tris, 1 mM EDTA, 0.2% Triton X-100, pH 7.5) as a control for total LDH release (Filion et al. Biochim Biophys Acta 1329:345–356, 1997). LDH was determined by commercial assay (Sigma-Aldrich).

Figure 8:
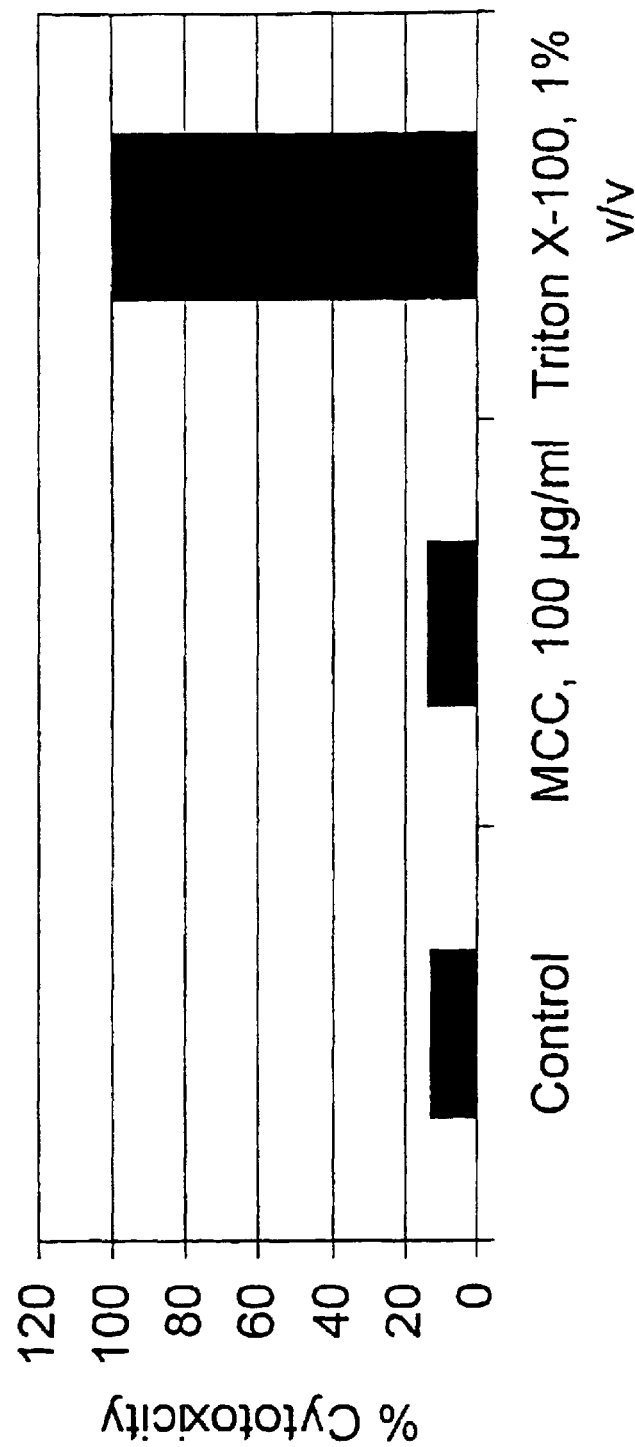
FIG. 8. Cytotoxicity of MCC.

As shown in FIG. 8, MCC was not cytotoxic to the B-16 melanoma cells. These data demonstrate that MCC does not act by disrupting the membrane of the cells, but that MCC acts directly on the B-16 melanoma cells to induce apoptosis.

EXAMPLE 15

Effects of M-DNA, MCC and DNase I Treated MCC on B-16 Melanoma Tumors in Mice

B-16 melanoma cells are implanted subcutaneously into 20 male nude BALB/c mice and allowed to grow for 10 days. The mice are divided into 4 groups and tumor mass is measured in each mouse. On day 0, Group 1 mice receive saline, Group 2 mice receive MCC, Group 3 mice receive M-DNA and Group 4 mice receive DNase I treated MCC. After 4 weeks of treatment, the mice are sacrificed and tumor mass is measured. Group 2 and Group 3 mice have less tumor mass than Group 1 and Group 4 mice.

EXAMPLE 16

Effects of M-DNA and MCC in Combination with Mitomycin-C on B-16 Melanoma Tumors in Mice B-16 melanoma cells are implanted subcutaneously into 30 male nude BALB/c mice and allowed to grow for 10 days. The mice are divided into 6 groups and tumor mass is measured in each mouse. On day 0, Group 1 mice receive saline, Group 2 mice receive M-DNA, Group 3 mice receive MCC, Group 4 mice receive mitomycin-C, Group 5 mice receive M-DNA and mitomycin-C and Group 6 mice receive MCC and mitomycin-C. After 4 weeks of treatment, the mice are sacrificed and the tumor mass and number of metastases are determined. Group 1 mice have the most tumor mass. Group 4 mice have less tumor mass than Group 1 mice. Group 2 and Group 3 mice have less tumor mass than Group 4 mice. Group 5 and Group 6 mice have the least tumor mass.

It should be understood, of course, that the foregoing relates only to a preferred embodiment of the present invention and that numerous modifications or alterations may be made therein without departing from the spirit and the scope of the invention as set forth in the appended claims.

We claim:

1. A method of inhibiting growth of cancer cells in an animal or a human having the cancer cells, comprising:
   (a) administering at the cancer cells in the animal or the human having the cancer cells a composition comprising *Mycobacterium phlei* (*M.phlei*)-DNA complexed on *Mycobacterium phlei* cell wall (MCC) and a pharmaceutically acceptable carrier; and
   (b) administering a chemotherapeutic agent to the animal or the human having the cancer cells, wherein the composition and the chemotherapeutic agent administered to the animal or the human having the cancer cells display an anti-cancer synergism so as to inhibit the growth of the cancer cells.

2. The method of claim 1, wherein the anti-cancer synergism is potentiation.

3. The method of claim 1, wherein the composition induces cell cycle arrest in the cancer cells, inhibits proliferation of the cancer cells, induces apoptosis in the cancer cells, or synchronizes cell cycles of the cancer cells.

4. The method of claim 1, wherein the cancer cells are leukemia, lymphoma or melanoma cancer cells.

5. The method of claim 1, wherein the cancer cells display resistance against one or more chemotherapeutic agents.

6. The method of claim 1, wherein the chemotherapeutic agent is administered before, after, or concurrently with the administration of the composition.

7. The method of claim 1, wherein the chemotherapeutic agent is a DNA cross-linking agent, a DNA depolymerizing agent, an antimetabolic agent, an anti-tumor antibiotic agent, a topoisomerase inhibiting agent or a tubulin stabilizing agent.

8. The method of claim 1, wherein the chemotherapeutic agent is mitomycin-C, 5-fluorouracil, or cisplatin.

9. A method of inhibiting growth of cancer cells in an animal or a human having the cancer cells comprising:
   (a) administering at the cancer cells in the animal or the human having the cancer cells a composition comprising *Mycobacterium phlei* (*M.phlei*)-DNA (M-DNA) and a pharmaceutically acceptable carrier; and
   (b) administering a chemotherapeutic agent to the animal or the human having the cancer cells, wherein the composition and the chemotherapeutic agent administered to the animal or the human having the cancer cells display an anti-cancer synergism so as to inhibit the growth of the cancer cells.

10. The method of claim 9, wherein the anti-cancer synergism is potentiation.

11. The method of claim 9, wherein the composition induces cell cycle arrest in the cancer cells, inhibits proliferation of the cancer cells, induces apoptosis in the cancer cells, or synchronizes cell cycles of the cancer cells.

12. The method of claim 9, wherein the cancer cells are leukemia, lymphoma or melanoma cancer cells.

13. The method of claim 9, wherein the cancer cells display resistance against one or more chemotherapeutic agents.

14. The method of claim 9, wherein the chemotherapeutic agent is administered before, after, or concurrently with the administration of th composition.

15. The method of claim 9, wherein the chemotherapeutic agent is a DNA cross-linking agent, a DNA depolymerizing agent, an antimetabolic agent, an anti-tumor antibiotic agent, a topoisomerase inhibiting agent or a tubulin stabilizing agent.

16. The method of claim 9, wherein the chemotherapeutic agent is mitomycin-C, 5-fluorouracil, or cisplatin.

17. A method of inhibiting growth of cancer cells in an animal or a human having the cancer cells, comprising:
   (a) administering at the cancer cells in the animal or the human having the cancer cells a composition comprising a mycobacterial DNA complexed on mycobacterial cell wall (BCC), and a pharmaceutically acceptable carrier; and
   (b) administering a chemotherapeutic agent to the animal or the human having the cancer cells, wherein the composition and the chemotherapeutic agent administered to the animal or the human having the cancer cells display an anti-cancer synergism so as to inhibit the growth of the cancer cells.

18. The method of claim 17, wherein the anti-cancer synergism is potentiation.

19. The method of claim 17, wherein the composition induces cell cycle arrest in the cancer cells, inhibits proliferation of the cancer cells, induces apoptosis in cells of the cancer cells, or synchronizes cell cycles of the cancer cells.

20. The method of claim 17, wherein the cancer cells are leukemia, lymphoma or melanoma cancer cells.

21. The method of claim 17, wherein the cancer cells display resistance against one or more chemotherapeutic agents.

22. The method of claim 17, wherein the chemotherapeutic agent is administered before, after, or concurrently with the administration of the composition.

23. The method of claim 17, wherein the chemotherapeutic agent is a DNA cross-linking agent, a DNA depolymerizing agent, an antimetabolic agent, an anti-tumor antibiotic agent, a topoisomerase inhibiting agent or a tubulin stabilizing agent.

24. The method of claim 17, wherein BCC is derived from *M. vaccae, M. chelonei, M. smegmatis, M. terrae, M. duvalii, M. tuberculosis, M. bovis* BCG, *M. avium, M. Szulgai, M. scrofulaceum, M. xenopi, M. kansaii, M. gastr, M. fortuitous,* or *M. asiaticum.*

25. A method of inhibiting growth of cancer cells in the animal or a human having the cancer cells comprising:

(a) administering at the cancer cells in the animal or the human having the cancer cells a composition comprising a mycobacterial DNA (B-DNA), and a pharmaceutically acceptable carrier; and (b) administering a chemotherapeutic agent to the animal or the human having the cancer cells, wherein the composition and the chemotherapeutic agent administered to the animal or the human having the cancer cells display an anti-cancer synergism so as to inhibit the growth of the cancer cells.

26. The method of claim 25, wherein the anti-cancer synergism is potentiation.

27. The method of claim 25, wherein the composition induces cell cycle arrest in the cancer cells inhibits proliferation of the cancer cells, induces apoptosis of the cancer cells, or synchronizes cell cycles of the cancer cells.

28. The method of claim 25, wherein the cancer cells are Leukemia, lymphoma or melanoma cancer cells.

29. The method of claim 25, wherein the cancer cells display resistance against one or more chemotherapeutic agents.

30. The method of claim 25, wherein the chemotherapeutic agent is administered before, after, or concurrently with the administration of the composition.

31. The method of claim 25, wherein the chemotherapeutic agent is a DNA cross-linking agent, a DNA depolymerizing agent, an antimetabolic agent, an anti-tumor antibiotic agent, a topoisomerase inhibiting agent or a tubulin stabilizing agent.

32. The method of claim 25, wherein B-DNA is derived from *M. vaccae, M. chelonei, M. smegmatis, M. terrae, M. duvalii, M. tuberculosis, M. bovis* BCG, *M. avium, M. Szulgai, M. scrofulaceum, M. xenopi, M. kansaii, M. gastr, M. fortuitous,* or *M. asiaticum.*

* * * * *